(12) United States Patent
Jiang et al.

(10) Patent No.: US 8,377,918 B2
(45) Date of Patent: Feb. 19, 2013

(54) APIGENIN FOR CHEMOPREVENTION, AND CHEMOTHERAPY COMBINED WITH THERAPEUTIC REAGENTS

(75) Inventors: Bing-Hua Jiang, Morgantown, WV (US); Jing Fang, Shanghai (CN)

(73) Assignee: ACC Therapeutics Inc, Gaithersburg, MD (US)

( * ) Notice: Subject to any disclaimer, the term of this patent is extended or adjusted under 35 U.S.C. 154(b) by 319 days.

(21) Appl. No.: 11/344,725

(22) Filed: Jan. 31, 2006

(65) Prior Publication Data

US 2006/0189680 A1 Aug. 24, 2006

Related U.S. Application Data

(60) Provisional application No. 60/648,548, filed on Jan. 31, 2005.

(51) Int. Cl.
*A01N 43/00* (2006.01)
*A01N 43/16* (2006.01)

(52) U.S. Cl. .......... 514/183; 514/456; 514/460

(58) Field of Classification Search ............ 514/183, 514/456, 460
See application file for complete search history.

(56) References Cited

U.S. PATENT DOCUMENTS

| 4,935,450 A * | 6/1990 | Cone, Jr. .......... 514/728 |
| 5,605,930 A * | 2/1997 | Samid .......... 514/510 |
| 6,441,025 B2 * | 8/2002 | Li et al. .......... 514/449 |
| 2004/0176384 A1 * | 9/2004 | Snyder et al. .......... 514/252.14 |

FOREIGN PATENT DOCUMENTS

WO    WO 03/026561    *    4/2003

OTHER PUBLICATIONS

Lin et al. ("Suppression of protein kinase C and nuclear oncogene expression as possible molecular mechanisms of cancer chemoprevention by apigenin and curcumin"; J Cell Biochem suppl. 1997;28-29:39-48).*

Torkin et al., "Induction of caspase-dependent, p53-mediated apoptosis by apigenin in human neuroblastoma"; Mol Cancer Ther. 2005;4:1-11.*

Gupta et al. ("Selective growth-inhibitory, cell-cycle deregulatory and apoptotic response of apigenin in normal versus human prostate carcinoma cells."; Biochem Biophys Res Commun. Oct. 5, 2001;287(4):914-20.).*

Van Dross et al., (The chemopreventive bioflavonoid apigenin modulates signal transduction pathways in keratinocyte and colon carcinoma cell lines.; J Nutr. Nov. 2003;133(11 Suppl 1):3800S-3804S.).*

Kobayashi et al. ("Effect of flavonoids on cell cycle progression in prostate cancer cells."; Cancer Lett. Feb. 8, 2002;176(1):17-23.).*

Zhang et al. ("Zhang"; JPET 299:426-433, 2001).*

AHFS (McVoy, Gerald K. AHFS Drug Information 1999. Bethesda, MD: American Society of Health-System Pharmacists, Inc., 1999).*

Caltagirone (Int. J. Cancer (2000); 87:595-600).*

Feng et al (Chinese Journal of Cancer (2003); 22(4):358-362). Chinese Language Publication.*

Feng et al (Chinese Journal of Cancer (2003); 22(4):358-362). English Translation.*

Woerdenbag et al (Planta Med. (1994); 60:434-437).*

* cited by examiner

*Primary Examiner* — James D Anderson
*Assistant Examiner* — Chris Simmons
(74) *Attorney, Agent, or Firm* — Lin Sun-Hoffman

(57) ABSTRACT

Apigenin is a nontoxic compound. The present invention is appropriate for apigenin use in people who have a high risk of getting cancer, and in people who have cancer through chemoprevention and chemotherapy, respectively. We showed that apigenin inhibited cancer cell proliferation, tumor growth and angiogenesis. Apigenin selectively inhibited proliferation and induced apoptosis of cancer cells, enhanced the sensitivity of different cancer cells to different therapeutic drugs including cisplatin and taxol. Apigenin also inhibits angiogenesis and tumor growth in human cancers, and inhibits angiogenic inducers such as hypoxia-inducible factor 1 (HIF-1) and vascular endothelial growth factor (VEGF). Apigenin inhibited expression of HIF-1 and VEGF through PI3K, AKT, p70S6K1 and HDM2 pathways, which are commonly observed in all kinds of human cancers. Thus, our results indicate that apigenin can be applied to various human cancers for chemoprevention, and for chemotherapy when combined with other therapeutic reagents.

8 Claims, 19 Drawing Sheets

A

B

FIG. 11. Apigenin greatly enhanced the Taxol in inducing cellular death (apoptosis).

FIG. 17B
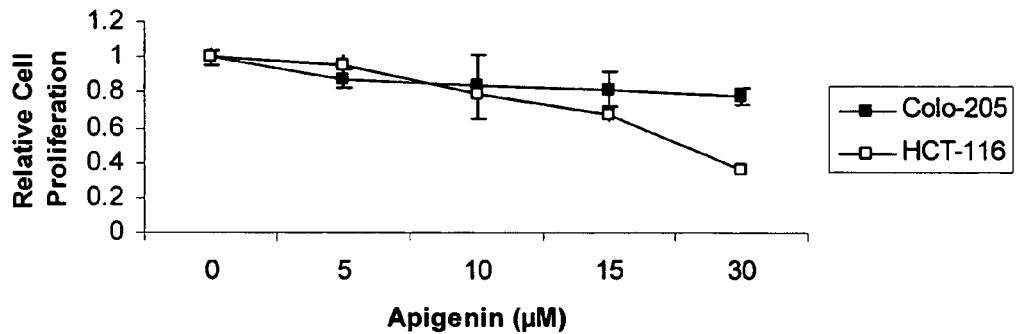
FIG. 17C
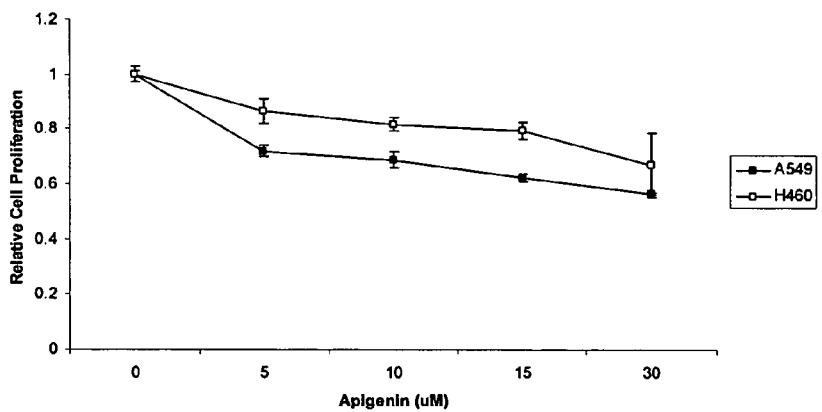
FIG. 17D. IC50 to inhibit proliferation of prostate, colon, and lung cancer cells.
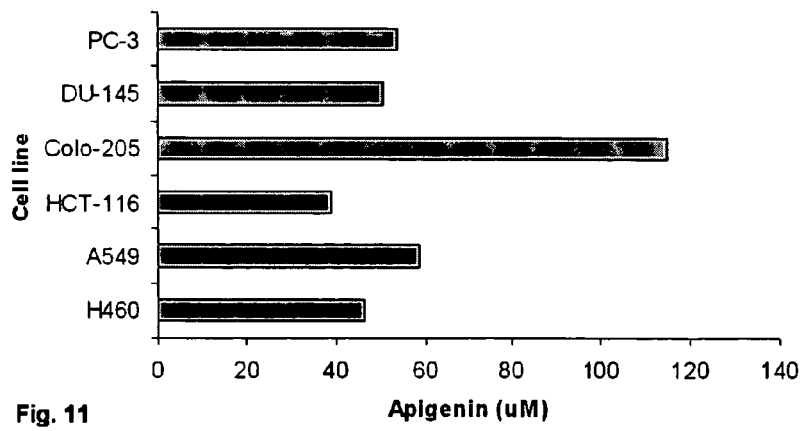
Fig. 11

FIG. 19B  Apigenin-induced senstivity of the DU-145 prostate cancer cell line to etoposide

APIGENIN FOR CHEMOPREVENTION, AND CHEMOTHERAPY COMBINED WITH THERAPEUTIC REAGENTS

RELATED APPLICATION

The invention claims priority from Provisional Application U.S. Ser. No. 60/648,548, filed on Jan. 31, 2005.

BACKGROUND OF THE INVENTION

Human cancer has become the leading cause of death for Americans under the age of 85. Although the overall cancer death rate has declined, approximately 470,000 people died of cancer in 2002. Lung cancer has the highest mortality rate of human cancers; prostate, ovarian, colon and breast cancers are also major causes of cancers for men and women. Although the five year survival rate has risen to 74 percent, 570,260 people are expected to die of cancer in 2005. Preventing and curing human cancer poses a challenge because many of the precursors to the disease are unknown. In many cancers, such as ovarian cancer, late diagnosis of the disease dramatically decreases survival rates. Chemotherapy is the primary treatment for cancers that have metastasized but it too poses problems. While in some cancers chemotherapy can prevent the spreading of the disease, slow cancer cell growth, and even cure the cancer, studies have shown that many types of cancer cells can develop resistance to chemotherapy drugs, causing a recurrence of the cancer and a higher mortality rate. Cancer prevention (chemoprevention) is another way to prevent human cancer. Although the mechanism(s) involved in the progression of human cancer are still unclear, increasing evidence in cancer prevention literature points toward the role of autocrine and paracrine factors in the development of cancer tumorigenesis and angiogenesis. Vascular endothelial growth factor (VEGF) and hypoxia-inducible factor 1 (HIF-1) play an important role in cancer development.

Apigenin is a nontoxic dietary flavonoid that has been used as a food supplement and antioxidant. Our study shows that apigenin can specifically inhibit several human cancer cell proliferation, decrease tumor growth and angiogenesis in vivo. Apigenin did not induce apoptosis of normal human cells at up to 40 µM apigenin. We also showed that apigenin inhibited VEGF expression which is required for tumor initiation and development. These data demonstrate that apigenin can be used for cancer prevention to inhibit the tumor initiation and development, and to inhibit human cancers.

Vascular endothelial growth factor (VEGF) plays an important role in tumor angiogenesis and growth. Angiogenesis is the formation of new blood vessels from pre-existing ones and is required for tumor growth and metastasis. Inhibiting the role of VEGF in promoting angiogenesis and tumor growth is a good target for cancer therapy. HIF-1 is overexpressed in many types of human cancers and it regulates VEGF expression at the transcriptional level. Therefore, inhibition of HIF-1 can potentially play a role in inhibiting angiogenesis and tumor growth.

Most caner patients especially in advanced disease stages require chemotherapy. Chemotherapy regime has proven to improve disease-free and overall survival in cancer patients. However, chemotherapeutic drugs can cause many side effects, including myelosuppression, immunosuppression, hepatotoxicity, nausea and vomiting, sore mouth, and diarrhea. The side effects can be very severe that interrupt the therapy or can even cause death. Several studies suggest that dietary supplementation with antioxidants can influence the response to chemotherapy as well as the development of adverse side effects that results from treatment with antineoplastic agents. Our studies show that, in addition to the antiangiogenic effects, apigenin synergizes with many chemotherapeutic drugs in inhibiting cancer cell growth. We propose that coadministration of apigenin may be of benefit for cancer treatment by reducing the doses of conventional chemotherapeutic reagents and thereby alleviates the side effects of chemotherapy, and apigenin treatment also confer the drug resistant tumors or cancer cells to be sensible to the same drug again.

SUMMARY OF THE INVENTION

The present invention is appropriate for prophylactic use in people who have a high risk of getting cancer and in people who have cancer. The dietary flavonoid apigenin is a very good compound to be used in the chemo-prevention and chemotherapy of many cancers when it is combined with other therapeutic reagents. It can be made as a pharmaceutical or as a food supplement to enhance therapeutic reagents for cancer therapy. Apigenin inhibits angiogenesis induced by cancer cells. For example, we showed that apigenin inhibited ovarian cancer cell proliferation and tumor formation. Apigenin selectively inhibited proliferation and induced apoptosis of cisplatin-resistant ovarian cancer cells, enhanced the sensitivity of ovarian and prostate cancer cells to therapeutic drugs such as cisplatin and taxol, and inhibited cancer cell growth.

Apigenin can be used to inhibit tumor angiogenesis and tumor growth in human cancers, and to inhibit angiogenic inducers such as hypoxia-inducible factor-1 and vascular endothelial growth factor. Apigenin inhibited VEGF expression at the transcriptional level in human cancer through expression of hypoxia-inducible factor $1\alpha$ (HIF-$1\alpha$). Apigenin inhibited expression of HIF-$1\alpha$ and VEGF through the PI3K/AKT/p70S6K1 and HDM2/p53 pathways. The increase of VEGF, HIF-1, and HDM2 expression and activation of PI3K/AKT/p70S6K1 are commonly observed in all kinds of human cancers. Thus, our results indicate that apigenin can be applied to all human cancers when combined with other therapeutic reagents for use in chemoprevention and for chemotherapy. Moreover, apigenin inhibited tube formation in vitro by endothelial cells, which is a common occurrence in all human cancers. Apigenin can enhance the chemotherapeutic effects of anti-cancer drugs currently used or to be used in the future.

Apigenin has strong inhibitory effects on various human cancer cells, including ovarian, prostate, colon, and lung cancers. In addition, apigenin greatly sensitizes cancer cells to many commonly used chemotherapy reagents, such as cisplatin, doxorubicin, etoposide, mitomycin C, fluorouracil, and taxol. These data implicate that the combination of apigenin with chemotherapeutic drugs can improve the effectiveness of conventional chemotherapy and alleviate the side effects, and also make the drug-resistant cancer cells to become treatable with lower doses with chemotherapeutic drugs.

These and other aspects of the present invention will become readily apparent upon further review of the following drawings and specification.

BRIEF DESCRIPTION OF THE DRAWINGS

The novel features of the described embodiments are specifically set forth in the appended claims; however, embodiments relating to the structure and process of making the present invention may best be understood with reference to the following description and accompanying drawings. The following experiments were used as a model system to demonstrate the application of apigenin, which can be applied to ovarian, lung, prostate, colon, and other human cancers.

FIG. 11. Apigenin enhanced the effects of taxol in inducing cell death. PC-3 prostate cancer cells and A2780/CP70 ovarian cancer cells were seeded in 96-well plates and incubated overnight. The old medium was discarded and fresh medium was added with different concentrations of taxol with or without 20 µM apigenin (Api) as indicated. After 48 h, cell survival was determined by means of MTT reduction assay. A, Apigenin treatment greatly enhanced taxol-induced PC-3 cell death with IC50: 50.33 nM, 11-fold less than that of taxol treatment alone (IC50: 577.19 nM). B, Apigenin treatment greatly enchanced taxol-induced A2780/CP70 cell death with IC50: 225.02 nM, 2 fold less than that of taxol treatment alone (IC50: 503.44 nM).

Similar reference characters denote corresponding features consistently throughout the attached drawings.

DETAILED DESCRIPTION OF PREFERRED EMBODIMENTS

Apigenin inhibits angiogenesis induced by cancer cells and can be used to inhibit tumor angiogenesis and tumor growth, and to inhibit angiogenic inducers such as vascular endothelial growth factor and hypoxia-inducible factor 1.

Apigenin (4',5,7,-trihydroxyflavone) is a common dietary flavonoid. It has low toxicity, is non-mutagenic, and is widely distributed in many fruits and vegetables, including parsley, onions, oranges, tea, chamomile, wheat sprouts, and in some seasonings (1). Apigenin is used as a health food supplement and recently has been shown to possess anti-tumor properties (2-5). Our data indicate apigenin's potential in the chemotherapeutic and chemopreventive treatment of cancers.

Human cancers have become the leading cause of death in America for people under the age of 85. The five year survival rate for most human cancers has decreased but the mechanism (s) of human cancer still remains unknown (6). While cisplatin, taxol and other therapeutic reagents are commonly used drugs in treating human cancers, cancer cells have been shown to gradually develop resistance to the therapeutic agents, eventually resulting in the death of the patients. Therefore it is very important to find a new reagent to enhance the therapeutic reagents for treating human cancers. Hence, apigenin is a promising drug when combined with therapeutic reagents for cancer chemotherapy.

Figure 1:
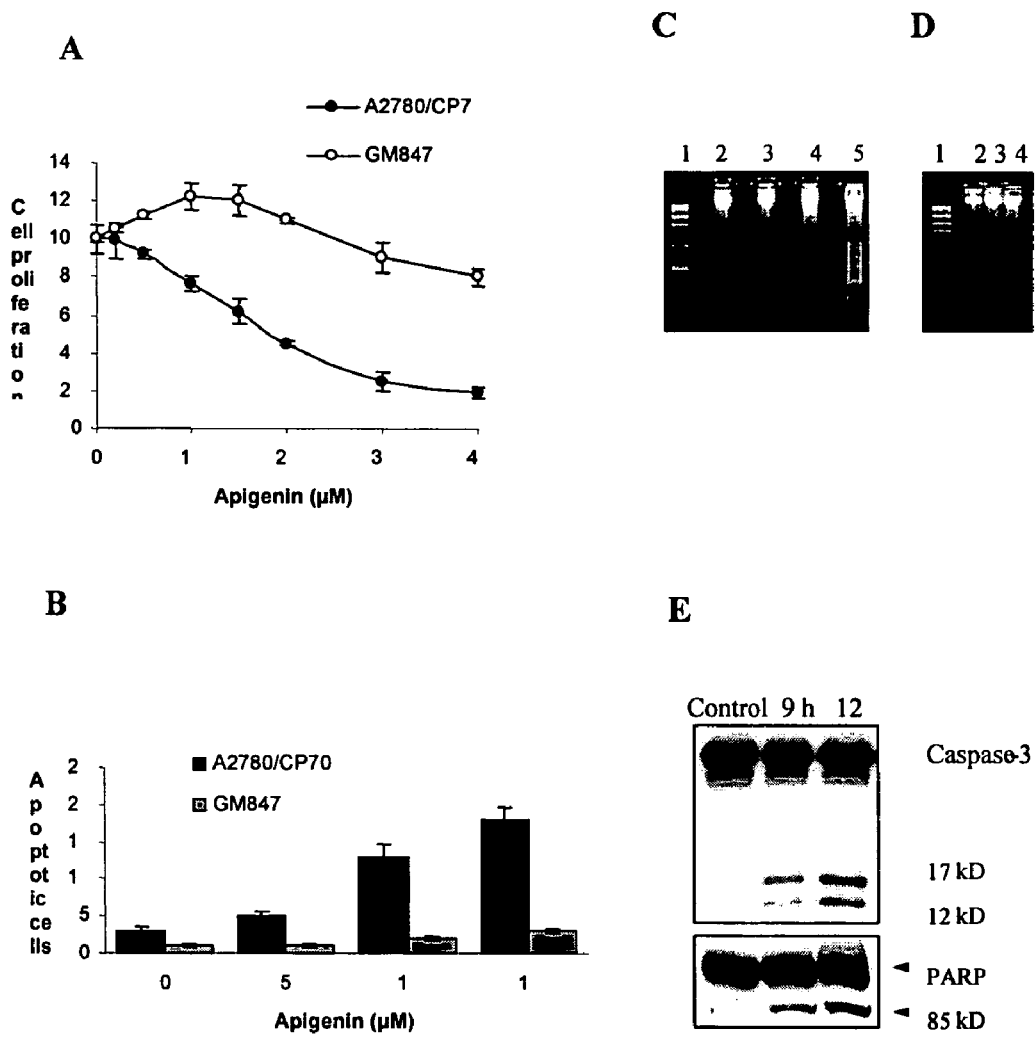
FIG. 1. Apigenin inhibited cell proliferation and specifically induced apoptosis of ovarian cancer cells. (A) A2780/CP70 cells and human fibroblast GM847 cells were seeded in 96-well plate at $4 \times 10^3$ cells per well and incubated overnight. The old medium was discarded and 100 µl of fresh medium with or without apigenin was added. The cells were incubated for 24 h. Cell proliferation was determined by MTT reduction. (B) A2780/CP70 or GM847 cells at 70-80% confluence were treated with apigenin for 24 h. Cells were trypsinized, harvested, washed once with PBS buffer, and stained using the Annexin-V-Folus Kit as per the manufacture's instructions. (C) A2780/CP70 cells were incubated with apigenin for 24 h. After incubation, all cells were collected and total DNA was isolated. Eight (8) µg of DNA was resolved on 1.8% agarose gel. Lane 1, DNA marker; lane 2, solvent alone; lane 3, 5 µM of apigenin; lane 4, 10 µM of apigenin; lane 5, 20 µM apigenin. (D) Treatment of GM847 cells was the same as that of 5D. Lane 1, marker; lane 2, the solvent control; lane 3, 10 µM apigenin; lane 4, 20 µM apigenin. (E) A2780/CP70 cells were incubated with 20 µM of apigenin. Cleavage of caspase-3 and PARP was detected by western-blot.
Figure 2:
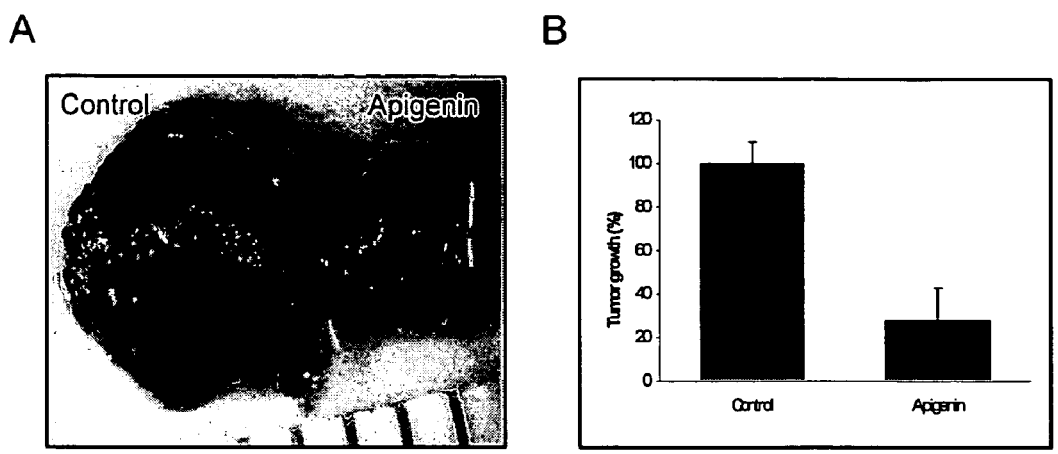
FIG. 2. Apigenin inhibited tumor growth. Ovarian cancer cells A2780/CP70 were planted into 9-days old fertilized chicken embryos and incubated for 9 days to allow the tumor formation. The formed tumors were harvested and cut into pieces of 9-10 mg weight, and immediately implanted into another 9-day old fertilized chicken embryo and incubated for 9 days. Meanwhile, the treated group received 7.5 µM apigenin and the control group received the same amount of solvent. In 9 days, the secondary tumor was cut and weighed. A, Representative of control and apigenin treated tumors; B, the data are mean±SD from two different experiments and each experiment had 20 embryos (10 for control and 10 for apigenin treatment).
Figure 3:
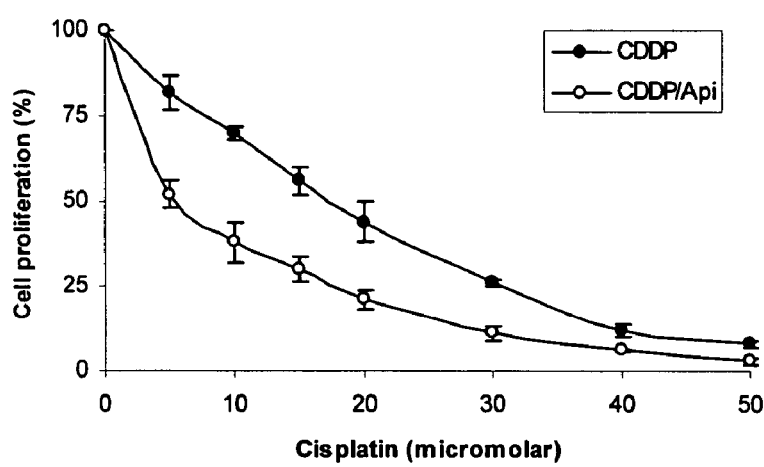
FIG. 3. Apigenin increased cisplatin sensitivity of A2780/CP70 cells. A2780/CP70 cells were seeded in 96-well plates and incubated overnight. The old medium was discarded and fresh medium with cisplatin (CDDP) in the presence or absence of apigenin (Api) was added. In 24 h, the cell proliferation was determined by means of MTT reduction method. Apigenin treatment greatly increased the cisplatin (CDDP) for inhibiting cell proliferation, decreased the concentration of CDDP in inhibiting 50% cell proliferation (IC50) to only ⅓ IC50 of solvent control.

Although apigenin has been shown to inhibit a few cancer cell lines, including colon, breast, and prostate cancer, its effects on enhancing chemotherapy and the chemotherapeutic effects of other agents when they are combined are unknown. In our research, we used the ovarian cancer cell lines A2780/CP70 and OVCAR-3 and prostate cancer cells PC-3 as model systems. We found that apigenin, at physiological concentrations, selectively inhibited cancer cells' proliferation and induced cell apoptosis (FIG. 1). Under the same experimental conditions, apigenin had little effects on the human normal fibroblast cells (FIG. 1). Apigenin may inhibit ovarian cancer cells' growth via inhibition of the (phosphoinositide 3-kinase) PI3K/AKT pathway, induction of p53, p21, and BAX, and activation of caspase cascades. Furthermore, we found that apigenin inhibited in vivo tumor growth of ovarian cancer cells (FIG. 2). We also found that apigenin enhanced the sensitivity of cisplatin-resistant A2780/CP70 cells to cisplatin treatment (FIG. 3), and the sensitivity of several human cancer cells to taxol, cisplatin, mitomycin C, doxorubicin and other therapeutic reagents.

Based on the daily dietary consumption of flavonoids, the concentration of apigenin used in this work is nontoxic and physiologically relevant in humans. Our results indicate that apigenin possesses the potential to inhibit cancer cell proliferation, tumor growth, and angiogenesis; and suggests a potential application of apigenin as a chemopreventive agent against human ovarian, lung, colon, prostate, and other cancers; and as chemotherapeutic agent to enhance the effects of other chemotherapeutic agents.

We found in this study that apigenin also possess the potential to inhibit tumor angiogenesis. Angiogenesis is the formation of new blood vessels. A tumor will not grow without new blood vessel formation because it needs newly-formed blood vessels to transport nutrients and oxygen (8,9). Angiogenesis is activated by many factors, among which is the vascular endothelial growth factor (VEGF) (9). Many cancer cells produce VEGF. The VEGF produced by cancer cells induces new blood vessel formation. The production of VEGF is mainly regulated by hypoxia-inducible factor 1 (HIF-1) (10). HIF-1 is a transcription factor, composed of HIF-1α and HIF-1β subunits. HIF-1α is unique to HIF-1 and is induced in response to a decrease in cellular O2 concentration and some growth factors. HIF-1 is identical to the aryl hydrocarbon nuclear translocator that forms a heterodimer with an aryl hydrocarbon receptor and is not regulated by cellular oxygen tension or growth factors. HIF-1 is overexpressed in many human cancers (11), and the levels of its activity in cells correlate with tumorigenicity and angiogenesis (12). VEGF and its upstream target HIF-1 are common targets in all cancer treatments. Thus, the combination of apigenin with therapeutic reagents can be applied to all cancer therapy.

Figure 4A:
FIG. 4. Apigenin greatly sensitized tumors induced by A2780/CP70 cells to CDDP, and enhanced CDPP in inhibiting angiogenesis. The A2780/CP70 cells were seeded into 100 mm dish and grown to 90-100% confluence. The cells were harvested, mixed with matrigel (2:1) by adding 2.5 µM cisplatin (CDDP), 10 µM apigenin, or 2.5 µM CDDP+10 µM apigenin; and implanted onto the CAM of 9-day old embryos. In 10 days, the tumors were harvested and weighed. The blood vessel numbers of the tumor were counted under×100. At least five areas were determined. The data are mean±SD from two experiments (n=8). A, representative tumor morphology; B, tumor weight; C, relative numbers of blood vessels.
Figure 4B:
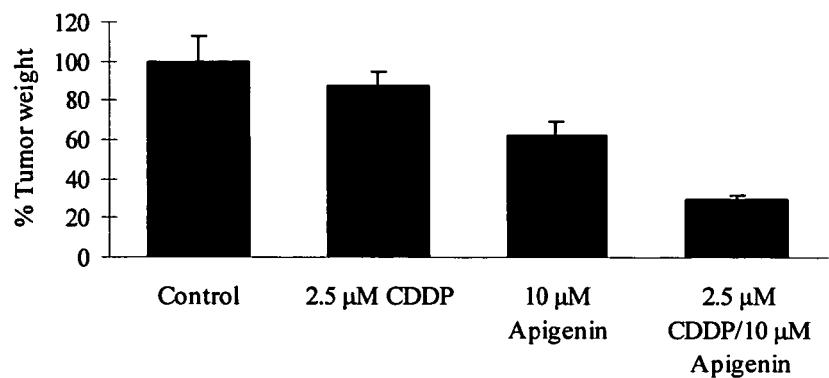
Figure 4C:
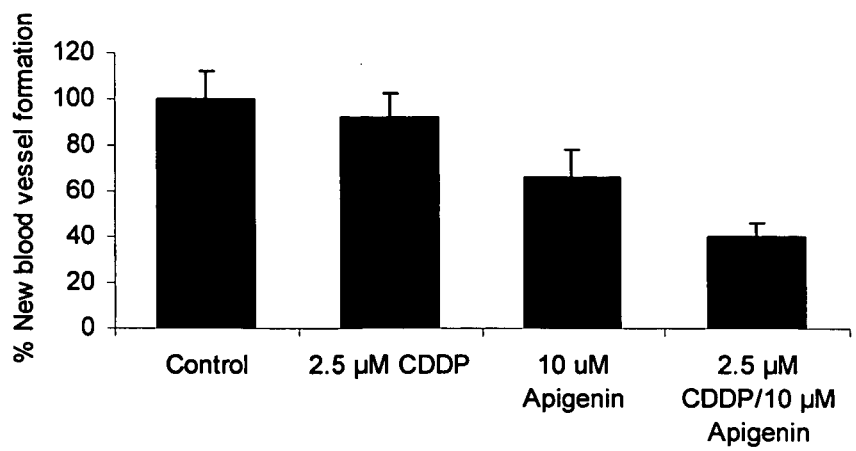
Figure 5:
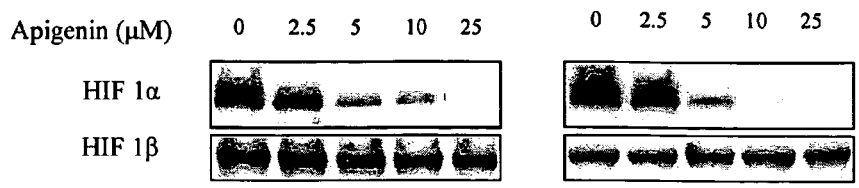
FIG. 5. Apigenin inhibited HIF-1 expression in OVCAR-3 and A2780/CP70 cells. A2780/CP70 and OVCAR-3 ovarian cancer cells were cultured to 80-90% confluence followed by a treatment with apigenin at the indicated concentrations. The cells treated with solvent alone were used as a control. HIF-1α and HIF-1β protein levels were detected by immunoblotting as described in Materials and Methods. GAPDH was used as an internal control to test the loading and transfer efficiency.
Figure 6:
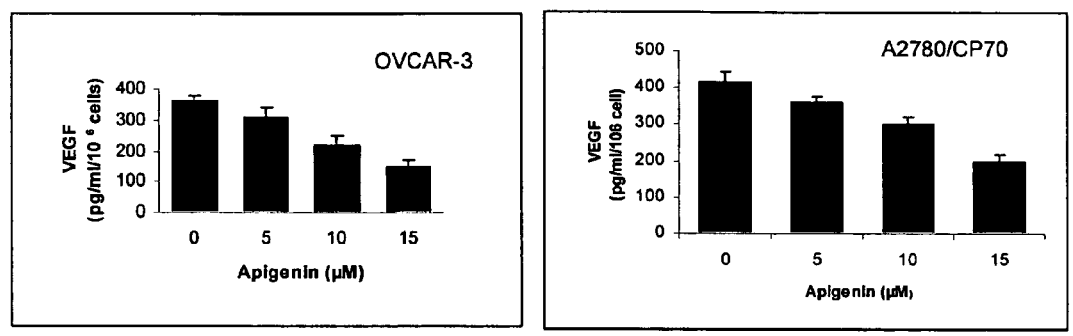
FIG. 6. Apigenin inhibited the expression of VEGF in ovarian cancer OVCAR-3 cells and A2780/CP70 cells. OVCAR-3 and A2780/CP70 cells were plated in 12-well plates and cultured to 90% confluence. The cells were switched to fresh medium containing apigenin and incubated for 15 h. The concentrations of VEGF in the supernatants were determined by ELISA method as described in Materials and Methods. The data are mean±SE from three independent experiments and each experiment was performed with triplicate cultures.
Figure 7:
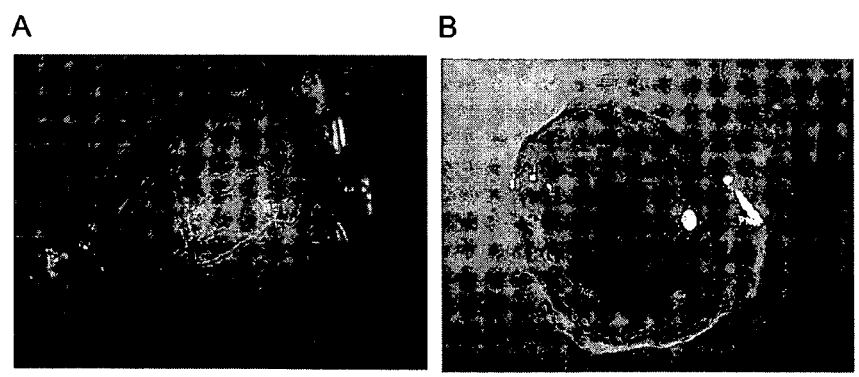
FIG. 7. Apigenin inhibited new blood vessel formation (angiogenesis) in tumors. A2780/CP70 ovarian cancer cells were mixed with Matrigel and implanted onto the chorioallantoic membrane (CAM) of a 9-day old embryo. In 100 h, the tumor was cut off and the newly-formed blood vessels on the back of the tumor were determined. A, Control; B, 15 µM apigenin treatment.

In reference to FIG. 4, apigenin greatly enhanced cisplatin-inhibited tumor formation induced by A2780/CP70 ovarian cancer cells. The results show that 2.5 µM cisplatin (CDDP) just slightly inhibited tumor growth since A2780/CP70 cells are CDDP resistant (FIG. 4). 10 µM apigenin inhibited A2780/CP70 tumor growth by 40%. The combination of CDDP and apigenin resulted in the inhibition of tumor growth by 70% (FIG. 4B). The results of blood vessel formation are consistent with those of our tumor assay. CDDP alone slightly inhibited the blood vessel formation induced by the cancer cells (FIG. 4C). Apigenin inhibited the blood vessel formation (angiogenesis) by 35%. When CDDP was combined with apigenin, the inhibition rate of angiogenesis increased to 60%. Taken together, our results suggest that apigenin can sensitize the A2780/CP70 ovarian cancer cells to CDDP, and enhance the effects of drug therapy used to treat human cancer. These data indicate that apigenin is useful in combination with other chemotherapy agents including CDDP for the therapeutic treatment of ovarian and other cancers.

Figure 8:
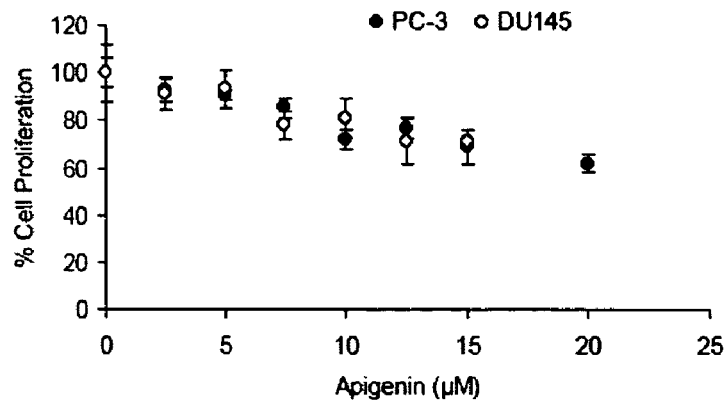
FIG. 8. Apigenin inhibited prostate cancer cell proliferation. Prostate cancer cells PC-3 and DU145 were seeded in 96-well plates at $1 \times 10^4$ cells/well. The old medium was discarded after 24 h and 100 µl of fresh medium with or without apigenin was added at the concentrations indicated. The cell proliferation was assayed by culturing the cells for 24 h, then adding 10 µl of MTT reagent with incubation for 2 h. The reaction was stopped by adding 100 µl of solubilization solution. The relative cell proliferation was obtained by the reading at 590 nm which was recorded in a spectrophotometer, and normalized to the value of control.

Apigenin inhibited cell proliferation and induced apoptosis in ovarian and prostate cancer cells in culture. The effects of apigenin on prostate cancer cell proliferation were determined using the PC-3 and DU145 cell lines. As shown in FIG. 8, apigenin alone inhibited both PC-3 and DU145 cell proliferation.

Figure 9:
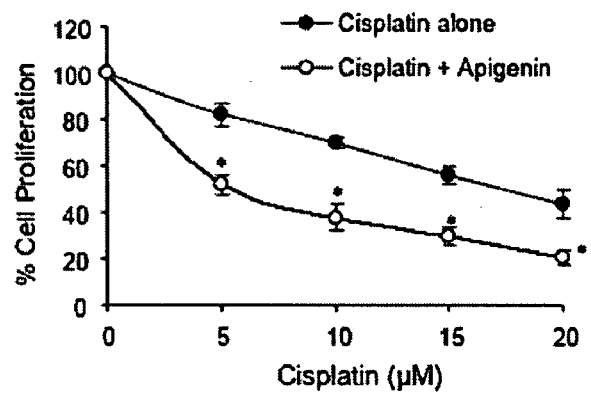
FIG. 9. Apigenin greatly enhanced the cisplatin effect in inhibiting ovarian and prostate cancer cell proliferation. A, Cisplatin-resistant ovarian cancer cell line A2780/CP70, and B, prostate cancer cells PC-3 were seeded in 96-well plates at $1 \times 10^4$ cells/well and incubated overnight. The cells were then provided with fresh medium containing either cisplatin alone at the concentrations indicated or cisplatin plus apigenin (10 µM). In 24 h, the cell proliferation was assayed by using a MTT assay kit. *indicates significant difference compared to cisplatin alone (p<0.01).
Figure 9:
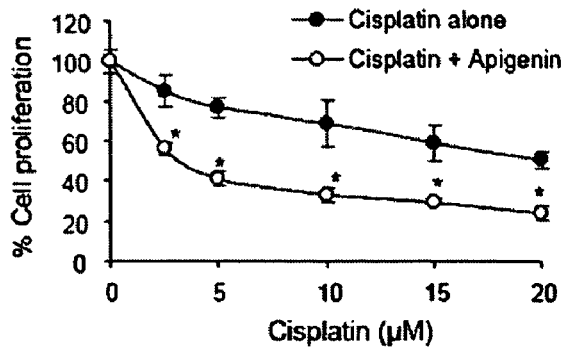

The effect of combining apigenin and cisplatin (a commonly used anti-cancer drug) on cancer cells was determined. The cisplatin-resistant ovarian cancer cell line A2780/CP70 and the prostate cancer cell line PC-3 served as a model. The concentration needed to inhibit 50% of A2780/CP70 cell proliferation was approximately 20 µM of cisplatin (IC50). The addition of 10 µM of apigenin decreased IC50 to 5 µM (4-fold reduction). Similar results were observed with PC-3 cells. As shown in FIG. 9, the addition of apigenin significantly increased the sensitivity of the PC-3 cells to cisplatin. In the presence of 10 µM of apigenin, only 3 µM of cisplatin resulted in a 50% inhibition of PC-3 cell proliferation (7-fold reduction). These results suggest that the combination of cisplatin with apigenin greatly enhanced the toxic effects of cisplatin on the cancer cells.

Figure 10:
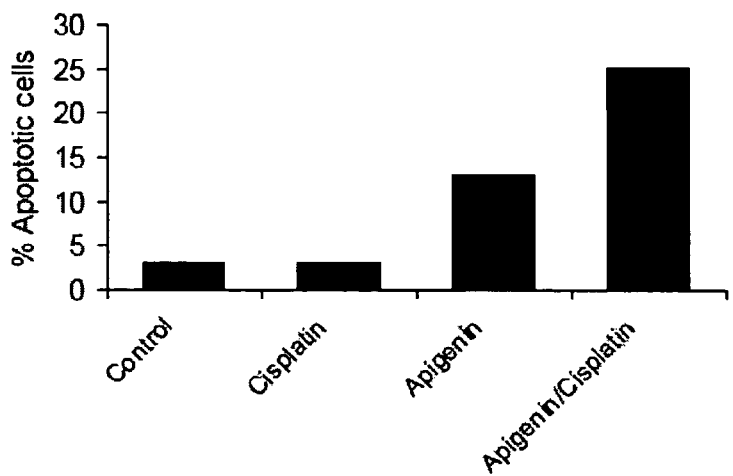
FIG. 10. Apigenin greatly enhanced cisplatin effect in inducing A2780/CP70 cell apoptosis. Apoptosis was monitored as the index of apigenin's effect on A2780/CP70 cells to cisplatin treatment. The cisplatin-resistant ovarian cancer A2780/CP70 cells were seeded in a petri dish. The next day, the cells were treated with cisplatin (10 µM), apigenin (10 µM), or apigenin (10 µM) plus cisplatin (10 µM) for 24 h. After treatment, the cells were collected and the relative cellular apoptosis was analyzed by Annexin V Kit (Roche), and compared to the control.
Figure 10:
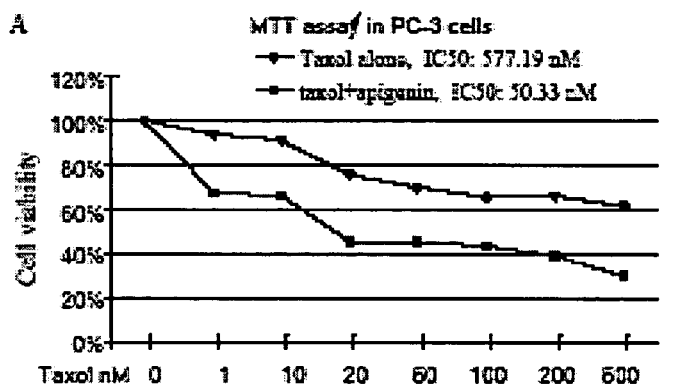
Figure 10:
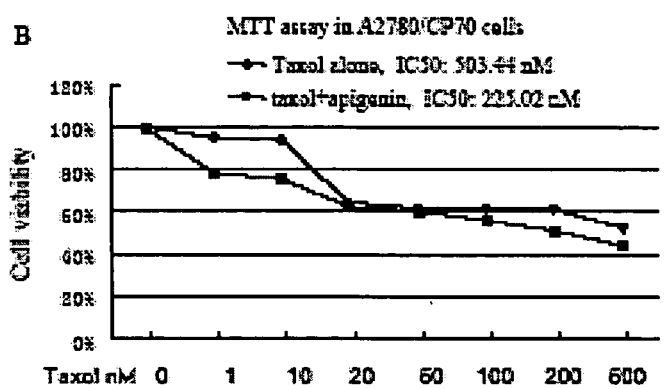

Apoptosis was monitored as another index of apigenin and cisplatin effects on cancer cell sensitivity. We used A2780/CP70 cells in this experiment. As shown in FIG. 10, 10 µM of cisplatin resulted in low levels of apoptosis of A2780/CP70 cells in 24 h. 10 µM of apigenin resulted in 12% of the cells undergoing apoptosis. A combination of cisplatin and apigenin led to 25% of the cells undergoing apoptosis (FIG. 10).

The effect of combining apigenin and taxol on cancer cell apoptosis was determined. The prostate cancer cell line PC-3 and the ovarian cancer cell line A2780/CP70 served as a model. As shown in FIG. 11A, the addition of 20 µM of apigenin significantly induced cellular apoptosis of PC-3 cells in the presence of taxol. The IC50 of cell viability decreased from 577.19 nM in the presence of taxol alone to 50.33 nM with the addition of apigenin. The addition of 20 µM of apigenin also induced the cellular apoptosis rate in A2780/CP70 cells (FIG. 11B). The IC50 of cell viability decreased from 503.44 nM with taxol alone to 225.02 nM with the addition of apigenin. These results suggest that the combination of taxol and apigenin greatly increased the rate of cancer cell death and chemotherapeutic effects.

Figure 12:
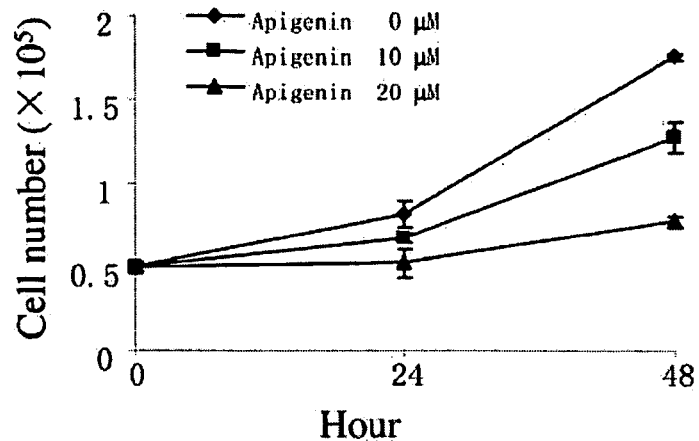
FIG. 12. Apigenin inhibited lung cancer cell A549 proliferation. A, A549 cells were seeded at $5 \times 10^5$ cells/well on a 24-well plate, and cultured overnight the day before the treatment. The old medium was discarded and 500 µl of fresh medium was added with various doses of apigenin (0, 10, and 20 µM). After 24 and 48 h, aliquots of cells were counted in triplicate using a hemocytometer to obtain cell number and proliferation rate.
Figure 13:
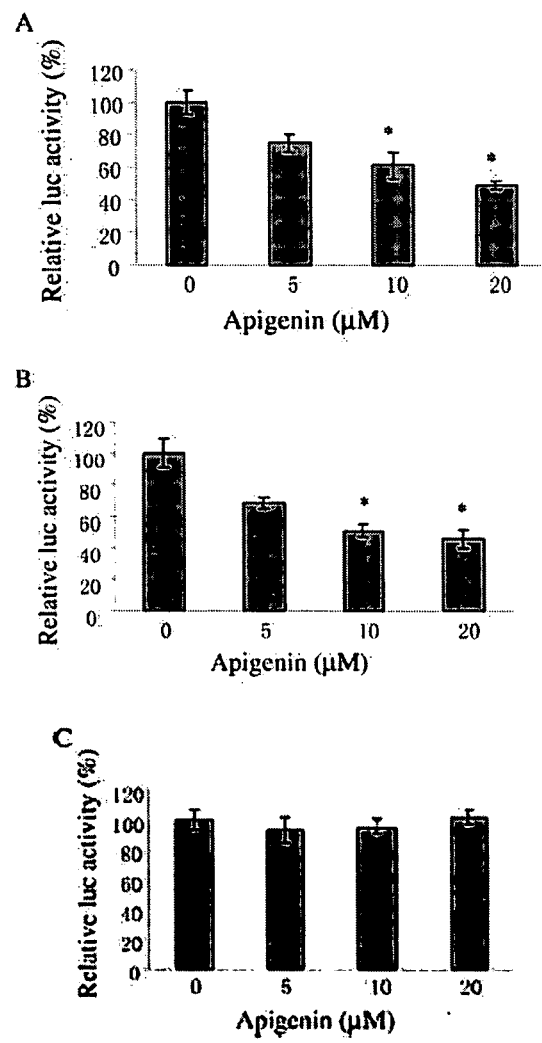
FIG. 13. Apigenin inhibited VEGF transcriptional activity through the HIF-1 DNA binding site. A549 cells were seeded on a six-well plate. When they reached 60 to 70% confluence, the cells were transfected using Lipofectamine reagent. A, A549 cells were cotransfected with 1 µg of pGL-StuI VEGF reporter and 0.3 µg of β-gal plasmid as described. The cells were cultured for 20 h, followed by treatment with apigenin at various doses (5, 10, and 20 µM) for 24 h. Cells were then lysed and the supernatants were used to assay Luc and β-gal activities. The relative luciferase activities in the cell extracts were assayed by the ratio of Luc/β-gal activity and normalized to the value in the solvent DMSO control. B, cells were cotransfected with 1 µg of pMAP11wt VEGF reporter and 0.3 µg of β-gal plasmid as described. Cells were treated with different doses of apigenin as described above. C, the cells were transfected with pMAP11mut VEGF reporter (with 3-bp substitution of pMAP11wt), and treated as above "B".
Figure 14:
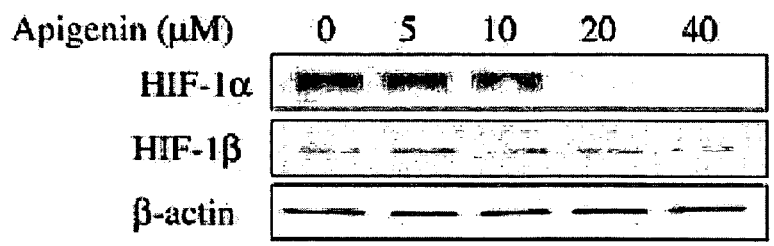
FIG. 14. Apigenin inhibited HIF-1α protein expression. A549 cells were seeded in 60-mm plates and cultured to 80 to 90% confluence. The cells were then treated with various doses of apigenin (5, 10, 20, and 40 µM) for 6 h. The cells treated with solvent alone were used as the control. Whole-cell extracts were subjected to immunoblotting analysis using antibodies specific for HIF-1α, HIF-1α, or β-actin.
Figure 15:
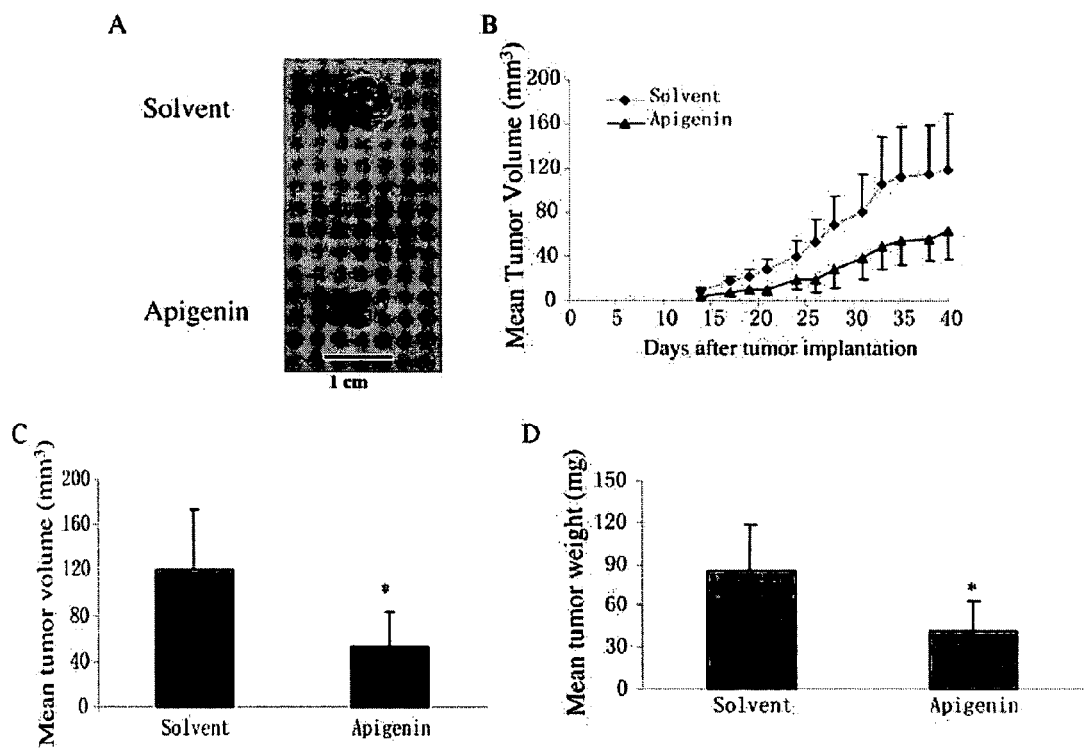
FIG. 15. Apigenin inhibited tumor growth in vivo. Nude mice were injected subcutaneously with $1\times10^6$ A549 cells in PBS buffer or with 15 µM apigenin. Each treatment group contained 10 mice. The mice were treated by intraperitoneal injection of PBS, or 3 mg/kg apigenin three times a week starting on day 4 to 40. The mice were euthanized on day 40. A, representative tumors from the control and apigenin-treated groups. Scale bar, 1 cm. B, tumor volumes were measured by the width and length of tumors from 10 mice in each treatment when tumors were visible. The mean±S.D. were obtained from 10 mice. C, the tumors were removed from mice, measured by the width and length, and analyzed as above. D, the mean±S.D. of the tumor weight. *, significant difference when compared with the solvent control ($p<0.05$).
Figure 16:
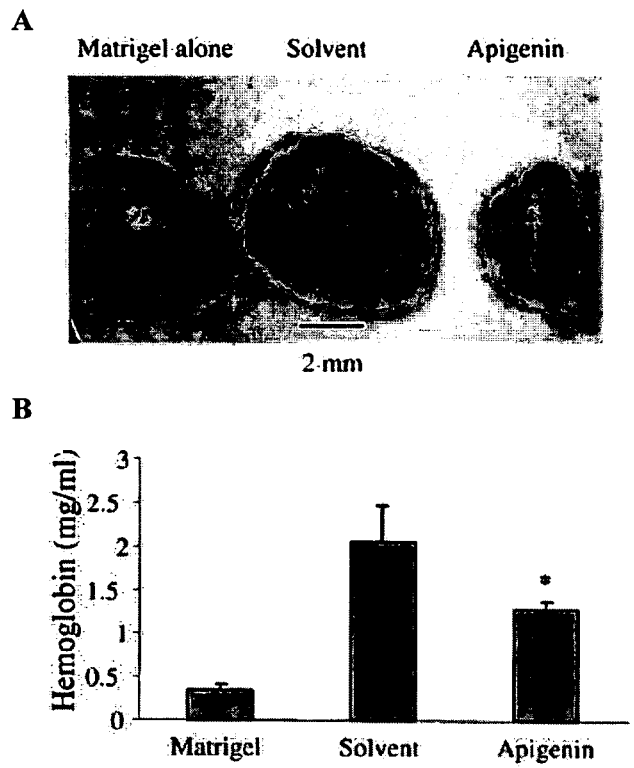
FIG. 16. Apigenin treatment inhibited A549 cell-induced tumor angiogenesis. B, nude mice were injected subcutaneously with Matrigel plugs on both sides, and each plug contained $3\times10^6$ A549 cells (0.1 ml) with 0.2 ml of Matrigel in the absence or presence of 15 µM apigenin. Each treatment group contained four mice. The mice were euthanized 15 days after implantation. Representative Matrigel plugs from the solvent- and apigenin-treated groups. C, D, the relative angiogenesis was analyzed by the levels of RBC hemoglobin, a surrogate marker, in the Matrigel plugs. The hemoglobin content was analyzed by adding 1×RBC lysis buffer (1 mM EDTA and 5 mM potassium/sodium phosphate buffer, pH 8-8.5) to a plug, followed by incubation at 4° C. overnight. Hemoglobin levels were determined by the Drabkin method by a commercial assay kit (Sigma) according to the manufacturer's instruction with some modification. Each treatment had four mice, each of which had an injection on two sides. Relative hemoglobin content is the hemoglobin level (milligrams) divided by the final volume of each plug. The data are the mean±S.E. of eight Matrigel plugs for each experiment. *, significant difference compared with the solvent control ($p<0.05$).

Apigenin significantly inhibits lung cancer cell proliferation (FIG. 12). Apigenin also dramatically suppresses VEGF transcriptional activation and HIF-1 protein expression in lung cancer cells (FIGS. 13, 14). Consistent with the in vitro data, apigenin has significant effects on tumor growth and tumor angiogenesis in vivo (FIGS. 15, 16).

Figure 17A:
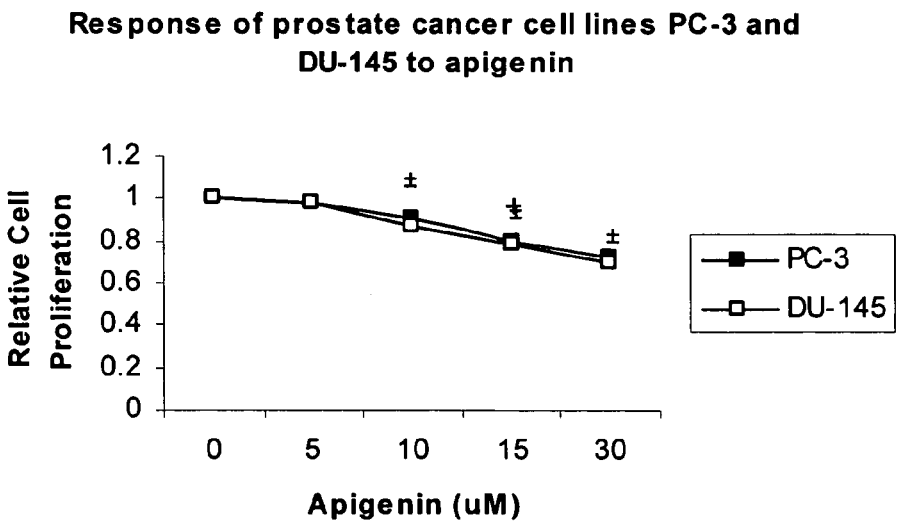
FIG. 17. Apigenin treatment inhibited the proliferation of prostate, colon, and lung cancer cells. A, the prostate cancer cells PC-3 and DU145; B, colon cancer cells Colo-205 and HCT-116; C, lung cancer cells A549 and H460 cells were plated at $1\times10^4$ cells per well in a 96 well plate in 100 µl of media. The cells were treated with indicated concentrations of apigenin in fresh media for 24 hours. The relative cell proliferation was assayed by MTT assay, and the value was normalized to that of the cells in the absence of apigenin. D, the concentrations of apigenin used to inhibit the 50% cell proliferation (IC50) was summarized.
Figure 18A:
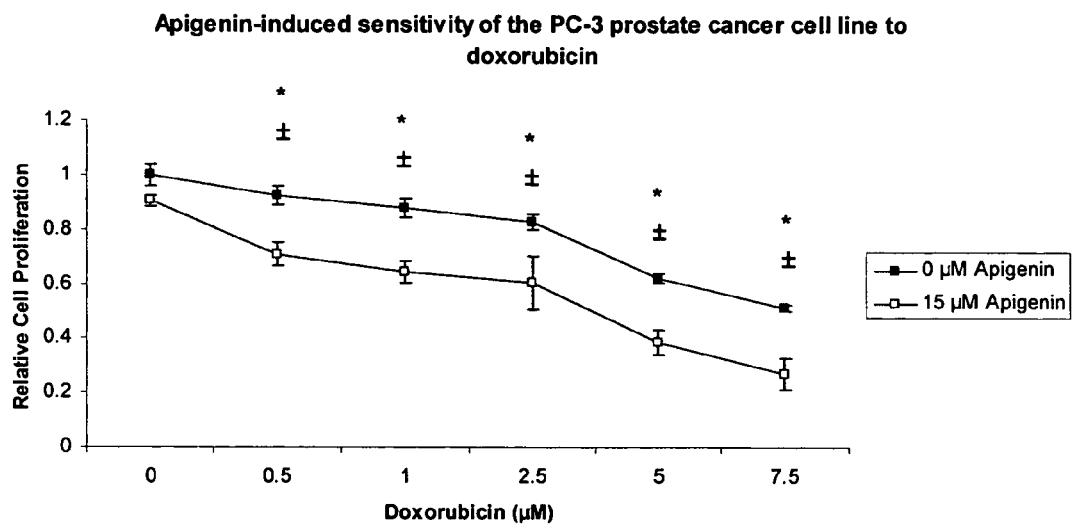
FIG. 18. Apigenin addition increased the sensitivity of prostate, colon, and lung cancer cells to the inhibition by doxorubicin treatment. A and B, the prostate cancer cells PC-3 and DU145; C, colon cancer cells Colo-205 and HCT-116; D, lung cancer cells A549 and H460 cells were plated at $1\times10^4$ cells per well in a 96 well plate in 100 µl of media. The cells were treated by the indicated concentrations of doxorubicin alone or in combination with 15 µM apigenin for 24 h. The cell proliferation was analyzed by MTT assay. (*, indicates the value treated by doxorubicin alone was significantly different when compared with doxorubicin treatment combined with apigenin, $p<0.05$; ±, indicates significant difference compared with the untreated control, $p<0.05$).
Figure 18B:
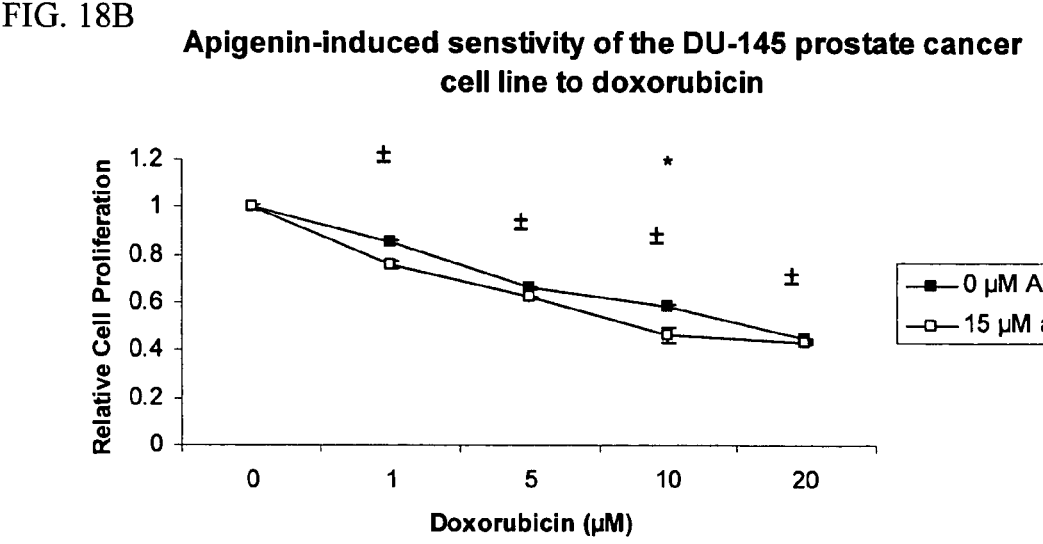
Figure 18C:
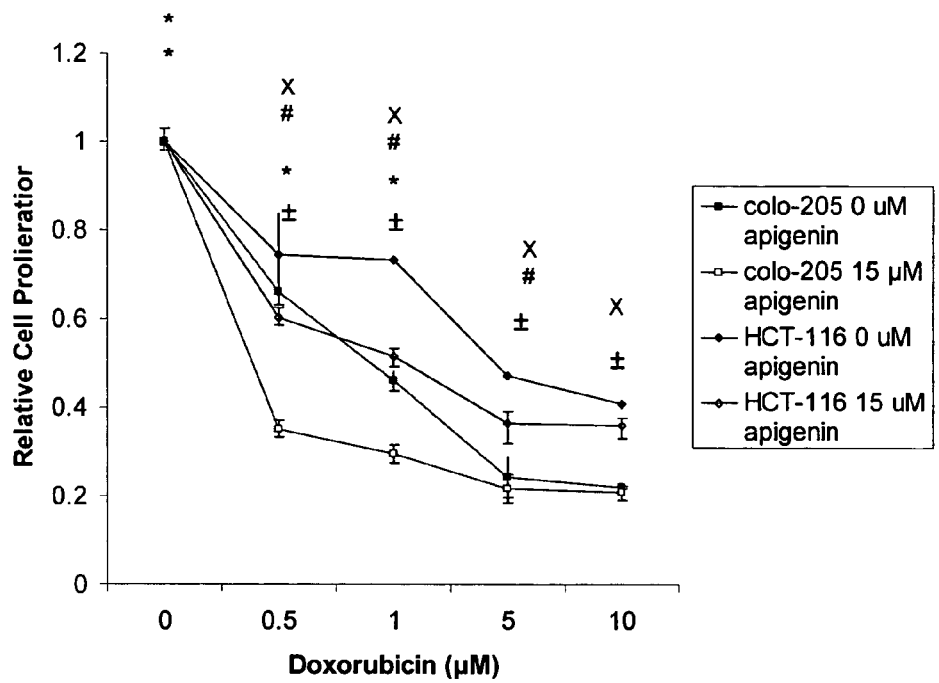
Figure 18D:
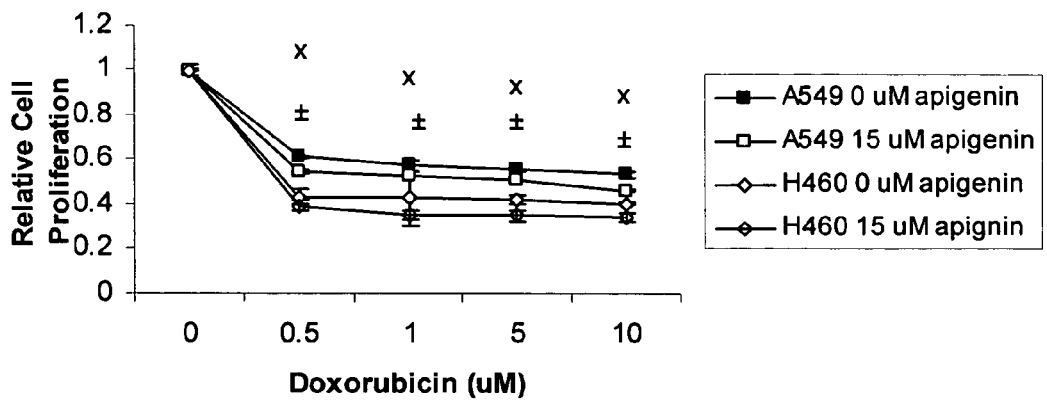
Figure 19A:
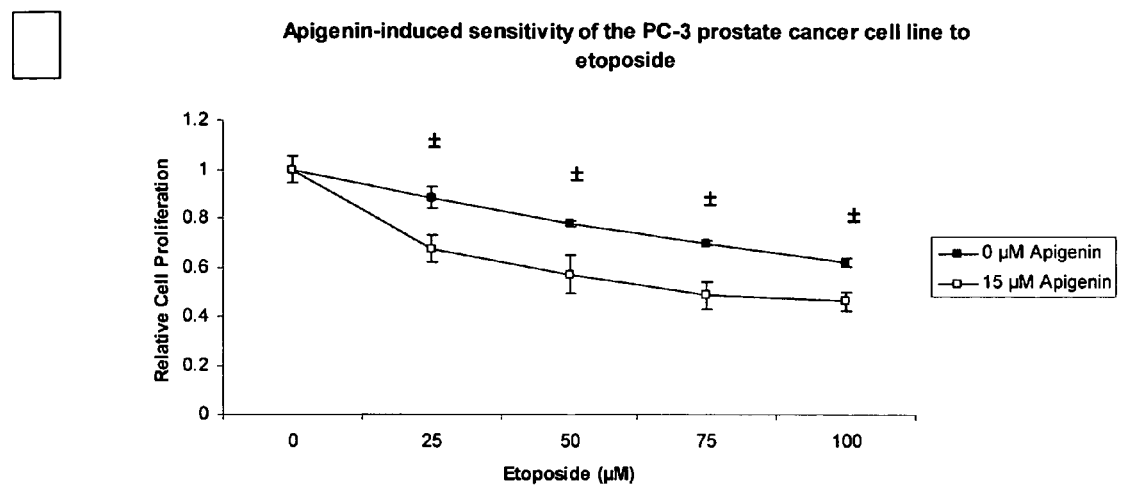
FIG. 19. Apigenin treatment increased the sensitivity of prostate cancer cells to etoposide treatment. A, prostate cancer cells PC-3; and B, DU145 cells were plated at $1\times10^4$ cells per well in a 96 well plate in 100 µl of media. The cells were treated by the indicated concentrations of etoposide alone or in combination with 15 µM apigenin for 24 h. Cell proliferation was examined by MTT assay. (±, indicates the value treated by doxorubicin alone was significantly different when compared with etoposide treatment combined with apigenin, $p<0.05$).
Figure 19A:
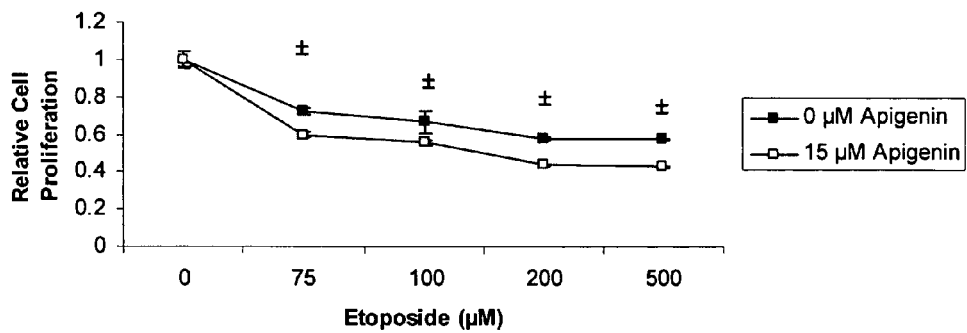
Figure 20A:
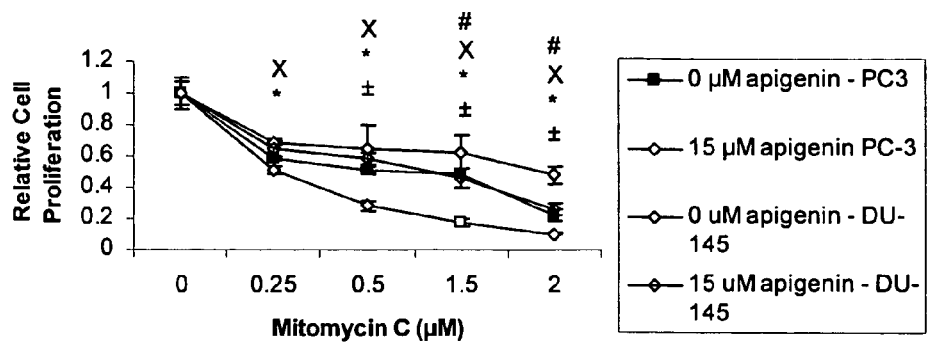
FIG. 20. Apigenin increased the sensitivity of prostate, colon, and lung cancer cells to the inhibition of mitomycin C treatment. A, the prostate cancer cells PC-3 and DU145; B, colon cancer cells Colo-205 and HCT-116; C, lung cancer cells A549 and H460 cells were plated at $1\times10^4$ cells per well in a 96 well plate. The cells were treated by the indicated concentrations of mitomycin C alone or in combination with 15 µM apigenin for 24 h. Cell proliferation was examined by MTT assay. Apigenin significantly increased the sensitivity of prostate, colon, and lung cancer cells to the inhibition of mitomycin C treatment ($p<0.05$). *, indicates the value treated by mitomycin C alone was significantly different for PC-3, Colo-205, or A549 cells when compared with treatment of the cells combined with apigenin ($p<0.05$); ±, indicates significant difference compared with the untreated control ($p<0.05$). $^x$, indicates the value treated by mitomycin C alone was significantly different for DU145, HCT-116, or H460 cells when compared with treatment of the cells combined with apigenin ($p<0.05$); #, indicates significant difference compared with the untreated control ($p<0.05$).
Figure 20B:
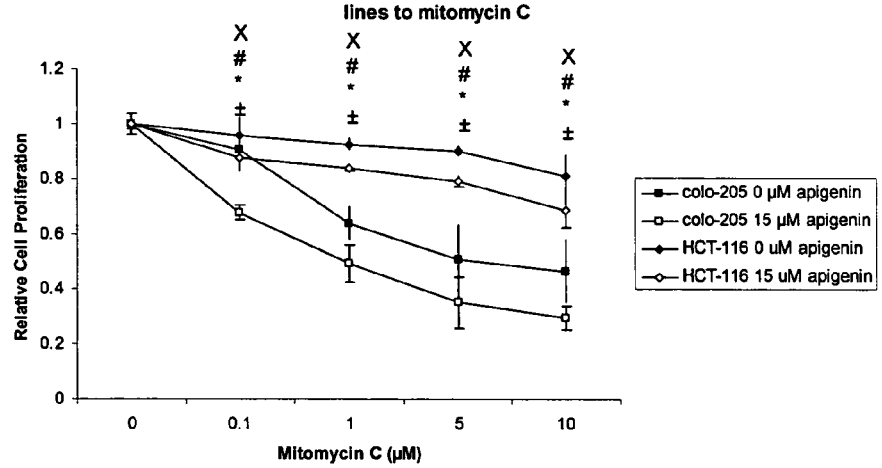
Figure 20C:
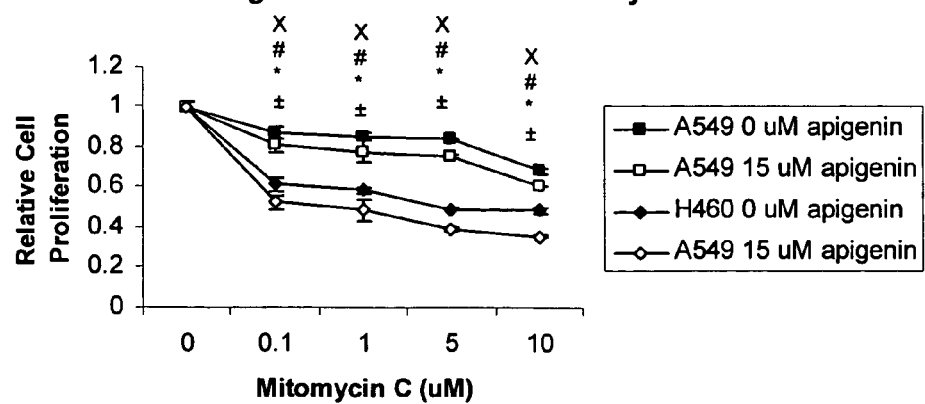
Figure 21A:
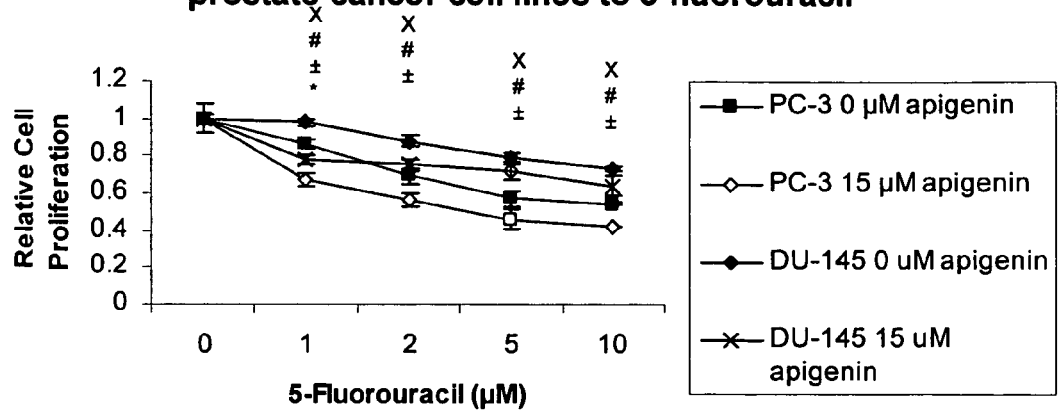
FIG. 21. Apigenin increased the sensitivity of prostate and colon cancer cells to 5-fluorouracil treatment. A, the prostate cancer cells PC-3 and DU145; B and C, colon cancer cells Colo-205 and HCT-116 were plated at $1\times10^4$ cells per well in a 96 well plate in 100 µl of media a day before the treatment. The cells were treated by the indicated concentrations of 5-Fluorouracil alone or in combination with 15 µM apigenin for 24 h. Cell proliferation was examined by MTT assay. *, indicates the value treated by 5-fluorouracil alone was significantly different for PC-3, Colo-205, or HCT-116 cells when compared with 5-fluorouracil treatment of the cells combined with apigenin ($p<0.05$); +, indicates significant difference compared with the untreated control ($p<0.05$). $^x$, indicates the value treated by 5-fluorouracil alone was significantly different for DU145 cells when compared with 5-fluorouracil treatment combined with apigenin (p<0.05).
Figure 21B:
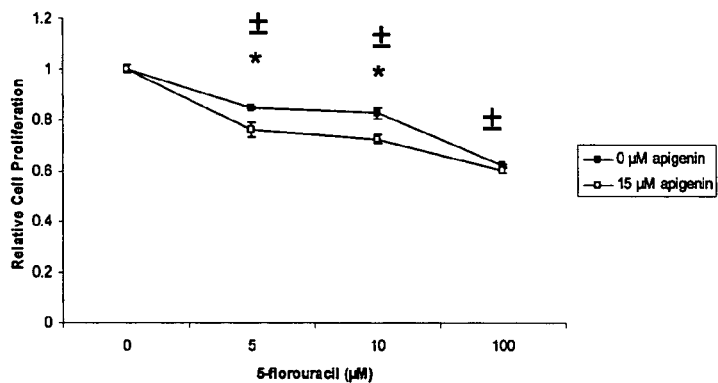
Figure 21C:
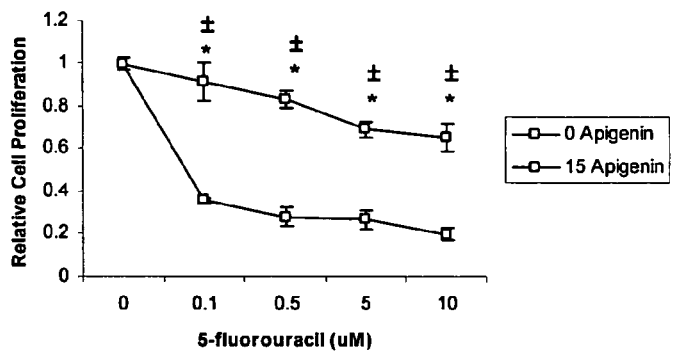
Figure 22A:
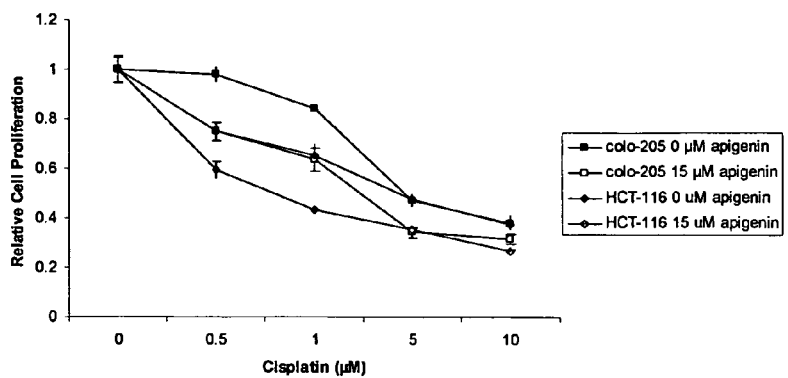
FIG. 22. Apigenin increased the sensitivity of colon and lung cancer cells to cisplatin treatment. A, colon cancer cells Colo-205 and HCT-116; B, lung cancer cells A549 and H460 cells were plated at $1\times10^4$ cells per well in a 96 well plate the day before the treatment. The cells were treated by the indicated concentrations of cisplatin alone or in combination with 15 µM apigenin for 24 h. Cell proliferation was examined by MTT assay. Similarly, apigenin treatment significantly increased the sensitivity of colon and lung cancer cells to cisplatin treatment.
Figure 22B:
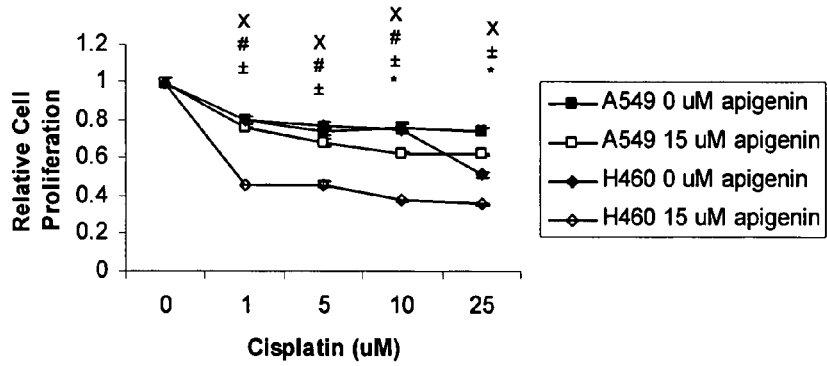

Apigenin shows strong inhibitory effects on cell proliferation of several other cancer cells, including prostate and colon cancers (FIG. 17). We have shown that apigenin exhibits anticancer effects on multiple cancer cell types, including ovarian, prostate, colon, and lung cancer, suggesting that apigenin has broad anticancer effects that may be useful for all human cancers.

Figure 23A:
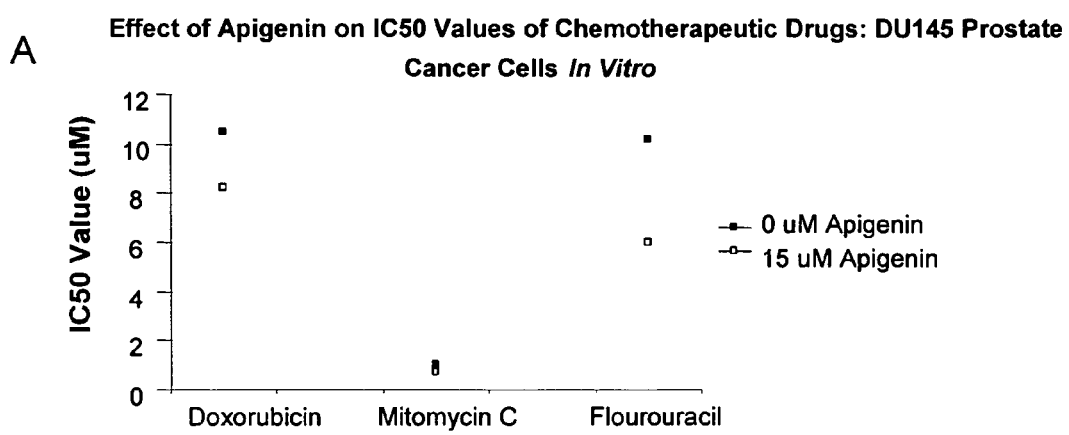
FIG. 23. Apigenin treatment increased the effect of doxorubicin, mitomycin C and 5-fluorouracil in inhibiting prostate cancer cells. The PC-3 and DU145 cells were treated by the indicated concentrations of doxorubicin, mitomycin C or 5-fluorouracil alone or treated by the drug combined with 15 µM apigenin for 24 h. Cell proliferation was examined by MTT assay. The concentrations of doxorubicin, mitomycin C and 5-fluorouracil in inhibiting 50% of cell proliferation (IC50) were obtained (FIG. 23). Apigenin treatment decreased the doses of doxorubicin, mitomycin C and 5-fluorouracil for inhibiting the cancer cell proliferation with much lower IC50.
Figure 23B:
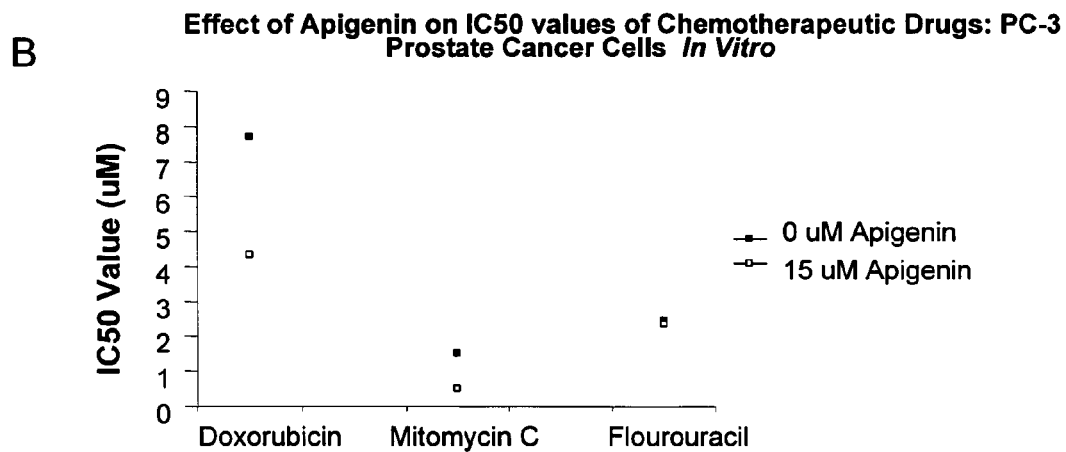
Figure 24A:
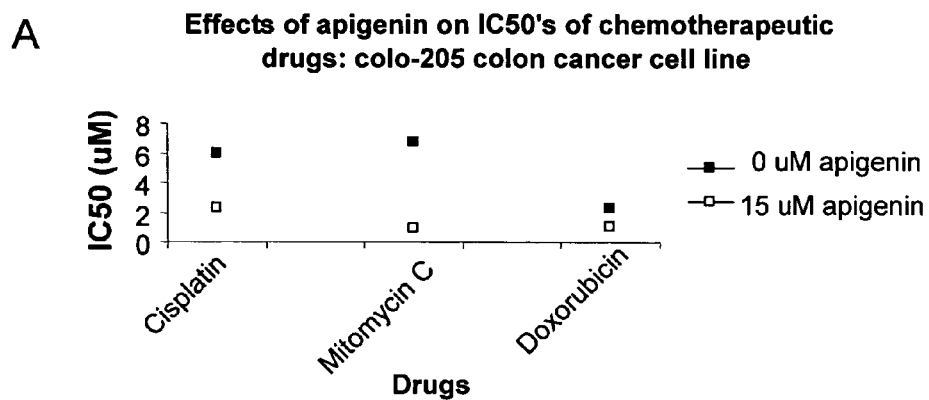
FIG. 24. Apigenin treatment reduces the IC50 values of cisplatin, mitomycin C and doxorubicin for inhibiting colon cancer cells. The IC50 values for inhibiting cell proliferation were calculated from cell proliferation assay as described above. Apigenin treatment greatly decreased the IC50 of cisplatin, mitomycin C and doxorubicin for inhibiting colon cancer cell proliferation as indicated in FIG. 24.
Figure 24B:
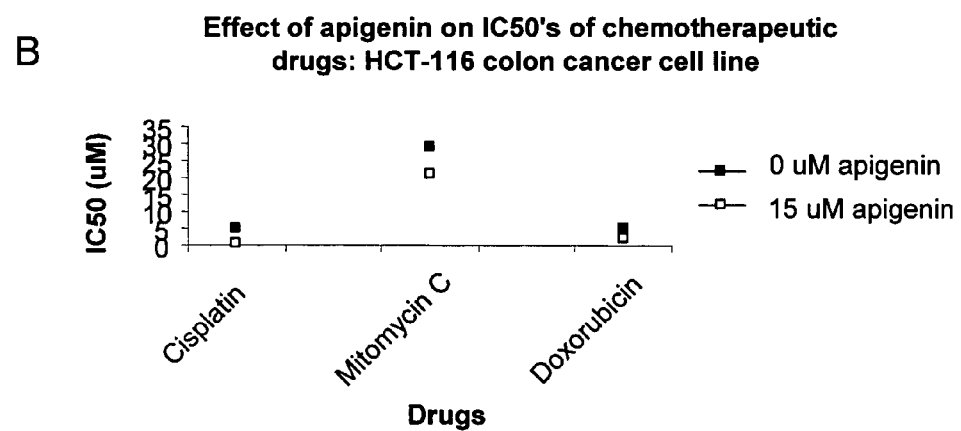
Figure 25A:
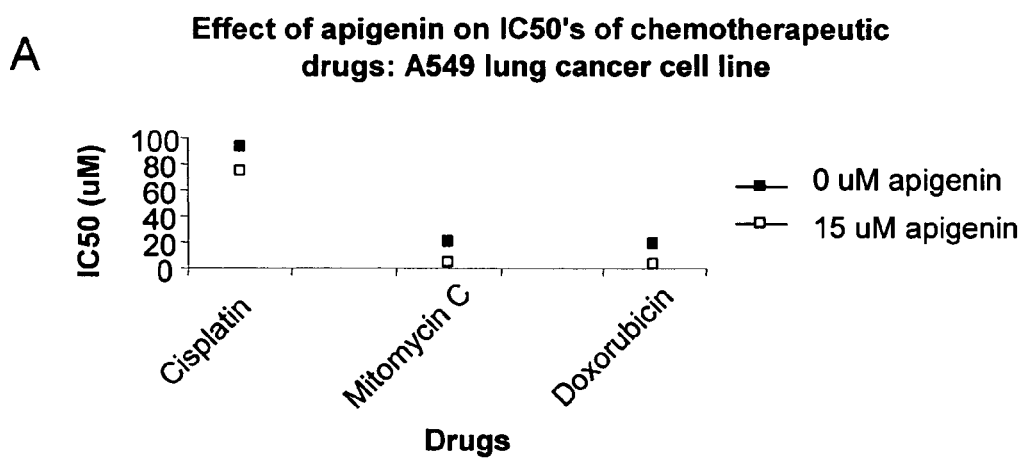
FIG. 25. Apigenin treatment reduces the IC50 values of cisplatin, mitomycin C, and doxorubicin for inhibiting lung cancer cells. The IC50 values from inhibiting 50% cell proliferation were calculated as described above. Apigenin treatment greatly decreased the IC50 values of cisplatin, mitomycin C, and doxorubicin for inhibiting lung cancer cells, A549 and H460 cells.
Figure 25B:
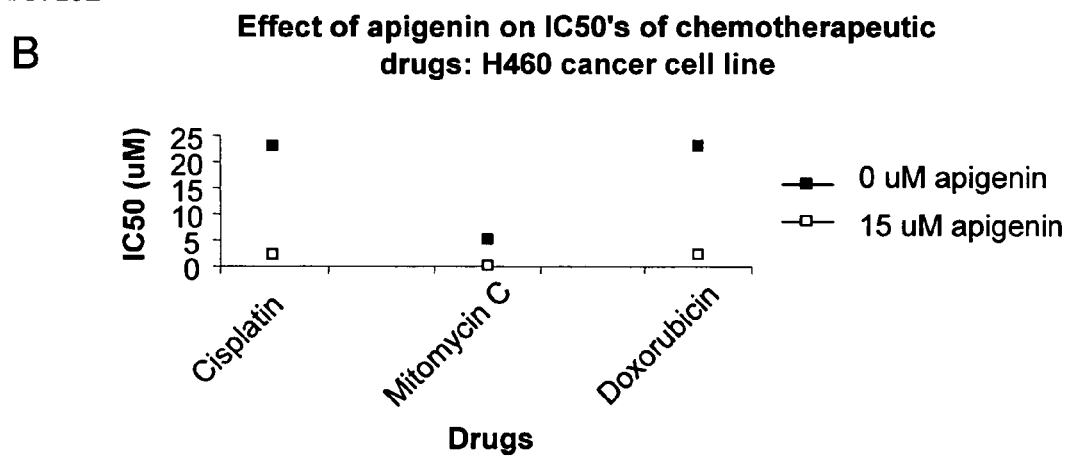

Apigenin was shown to increase the sensitivity of prostate, colon, and lung cancer cells to many commonly used chemotherapy reagents, such as doxorubicin, etoposide, mitomycin C, fluorouracil, taxol, and cisplatin (FIGS. 11,18-22). These data suggest that apigenin may synergize with most or all the chemotherapeutic drugs for cancer treatment. Importantly, apigenin greatly decreases the doses of many chemotherapy drugs in inhibiting cancer cell growth. Apigenin reduces the IC50 (inhibiting 50% cell proliferation) of fluorouracil by 70% of inhibiting DU145 prostate cancer cells (FIG. 23A), and reduces the IC50 of doxorubicin by 2-fold on PC-3 prostate cancer cells (FIG. 23B). Apigenin decreases the IC50 of cisplatin by 3-fold, and mitomycin C by 7-fold on colo-205 colon cancer cell (FIG. 24A). The IC50 of cisplatin and doxorubicin for inhibiting H460 lung cancer cells was decreased by 20-fold by the combination of apigenin treatment with cisplatin and doxorubicin, respectively (FIG. 25B). Taken together, our data suggest that apigenin can improve the effectiveness and decrease the doses of conventional chemotherapeutic drugs for cancer treatment, and therefore has great clinical significance for the therapeutic regime for many or all human cancers.

It is to be understood that the present invention is not limited to the embodiments described above, but encompasses any and all embodiments within the scope of the following claims.

REFERENCES

1. Duthie, G., Crozier, A. (2000) Plant-derived phenolic antioxidants. Curr. Opin. Clin. Nutr. Metab Care 3, 447-451.

2. Gupta, S., Afaq, F., Mukhtar, H. (2001) Selective growth-inhibitory, cell-cycle deregulatory and apoptotic response of apigenin in normal versus human prostate carcinoma cells. Biochem. Biophys. Res. Commun. 287, 914-920.

3. Wang, W., Heideman, L., Chung, C. S., Pelling, J. C., Koehler, K. J., Birt, D. F. (2000) Cell-cycle arrest at G2/M and growth inhibition by apigenin in human colon carcinoma cell lines. Mol. Carcinog. 28, 102-110.

4. Yin, F., Giuliano, A. E., Law, R. E., Van Herle, A. J. (2001) Apigenin inhibits growth and induces G2/M arrest by modulating cyclin-CDK regulators and ERK MAP kinase activation in breast carcinoma cells. Anticancer Res. 21, 413-420.

5. Fotsis, T., Pepper, M. S., Aktas, E., Breit, S., Rasku, S., Adlercreutz, H., Wahala, K., Montesano, R., Schweigerer, L. (1997) Flavonoids, dietary-derived inhibitors of cell proliferation and in vitro angiogenesis. Cancer Res. 57, 2916-2921.

6. Perez, R. P., Godwin, A. K., Hamilton, T. C., and Ozols, R. F. 1991. Ovarian cancer biology. Semin. Oncol. 18:186-204.

7. Greenlee, R. T., Hill-Harmon, M. B., Murray, T., and Thun, M. 2001. Cancer statistics, 2001. CA Cancer J. Clin. 51:15-36.

8. Folkman, J. (2002) Role of angiogenesis in tumor growth and metastasis. Semin. Oncol. 29, 15-18.

9. Plate, K. H., Breier, G., Weich, H. A., Risau, W. (1992) Vascular endothelial growth factor is a potential tumour angiogenesis factor in human gliomas in vivo. Nature 359, 845-848.

10. Semenza, G. L. (2000) Hypoxia, clonal selection, and the role of HIF-1 in tumor progression. Crit Rev. Biochem. Mol. Biol. 35, 71-103.

11. Zhong, H., De Marzo, A. M., Laughner, E., Lim, M., Hilton, D. A., Zagzag, D., Buechler, P., Isaacs, W. B., Semenza, G. L., Simons, J. W. (1999) Overexpression of hypoxia-inducible factor 1alpha in common human cancers and their metastases. Cancer Res. 59, 5830-5835.

12. Maxwell, P. H., Dachs, G. U., Gleadle, J. M., Nicholls, L. G., Harris, A. L., Stratford, I. J., Hankinson, O., Pugh, C. W., Ratcliffe, P. J. (1997) Hypoxia-inducible factor-1 modulates gene expression in solid tumors and influences both angiogenesis and tumor growth. Proc. Natl. Acad. Sci. U.S.A 94, 8104-8109.

13. Conklin K A. (2000) Dietary antioxidants during cancer chemotherapy: impact on chemotherapeutic effectiveness and development of side effects. Nutr Cancer. 37, 1-18.

What is claimed is:

1. A method of inhibiting or treating a chemotherapy-resistant solid tumor in a subject, comprising administering to said subject a composition comprising a) a therapeutically effective amount of apigenin, b) a therapeutically effective amount of a chemotherapeutic agent, and c) a pharmaceutically acceptable carrier

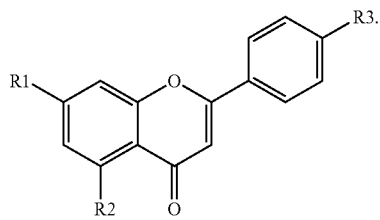

2. The method of claim 1, wherein the chemotherapeutic agent is selected from the group consisting of cisplatin, taxol, doxorubicin, etoposide, mitomycin C and 5-FU.

3. The method of claim 1, wherein the solid tumor is lung cancer.

4. The method of claim 1, wherein the solid tumor is ovarian cancer.

5. The method of claim 1, wherein the solid tumor is colon cancer.

6. The method of claim 2, wherein the chemotherapeutic agent comprises cisplatin.

7. The method of claim 1, wherein the solid tumor is ovarian cancer and the chemotherapeutic agent comprises cisplatin.

8. A method of inhibiting or treating a chemotherapy-resistant ovarian cancer in a subject, comprising administering to said a subject a composition comprising a) a therapeutically effective amount of apigenin, b) a therapeutically effective amount of cisplatin and c) a pharmaceutically acceptable carrier.

* * * * *